US010766021B2

(12) United States Patent
Lee et al.

(10) Patent No.: US 10,766,021 B2
(45) Date of Patent: Sep. 8, 2020

(54) PROPYLENE DIRECT OXIDATION REACTION CATALYST, METHOD FOR PREPARING SAME, AND METHOD FOR PREPARING PROPYLENE OXIDE THROUGH PROPYLENE DIRECT OXIDATION REACTION USING SAME

(71) Applicants: LOTTE CHEMICAL CORPORATION, Seoul (KR); SEOUL NATIONAL UNIVERSITY R&DB FOUNDATION, Seoul (KR)

(72) Inventors: Joong Won Lee, Daejeon (KR); Hyung Ki Min, Cheongju-si (KR); Young Jong Seo, Daejeon (KR); In Kyu Song, Seoul (KR); Eo Jin Lee, Cheongju-si (KR); Jong Heop Yi, Seoul (KR)

(73) Assignees: Lotte Chemical Corporation, Seoul (KR); Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 16/327,262

(22) PCT Filed: Aug. 22, 2017

(86) PCT No.: PCT/KR2017/009147
§ 371 (c)(1),
(2) Date: Feb. 21, 2019

(87) PCT Pub. No.: WO2018/038505
PCT Pub. Date: Mar. 1, 2018

(65) Prior Publication Data
US 2019/0184377 A1 Jun. 20, 2019

(30) Foreign Application Priority Data
Aug. 22, 2016 (KR) .................. 10-2016-0106152

(51) Int. Cl.
C07D 301/10 (2006.01)
B01J 23/68 (2006.01)
(Continued)

(52) U.S. Cl.
CPC ............ B01J 23/687 (2013.01); B01J 21/066 (2013.01); B01J 23/28 (2013.01); B01J 23/30 (2013.01);
(Continued)

(58) Field of Classification Search
CPC . B01J 23/687; B01J 23/28; B01J 23/30; B01J 23/68; B01J 23/50; B01J 35/1009;
(Continued)

(56) References Cited

U.S. PATENT DOCUMENTS 3,439,001 A 4/1969 Pell et al.
5,210,354 A 5/1993 Dubner et al.
(Continued)

FOREIGN PATENT DOCUMENTS

CA 1282772 C 4/1991
JP 2013-505995 A 2/2013
(Continued)

OTHER PUBLICATIONS

Hu, Zhen-Ming et al.; "Oxidation mechanism of propylene on an Ag surface: dipped adcluster model study"; Surf. Sci.; vol. 401; 1998; pp. 371-391.
(Continued)

*Primary Examiner* — Taylor V Oh
(74) *Attorney, Agent, or Firm* — Lewis Roca Rothgerber Christie LLP

(57) ABSTRACT

Disclosed is a propylene direct oxidation reaction catalyst capable of preparing a propylene oxide from propylene and oxygen at a higher yield than catalysts prepared by conventional methods, by applying a specific transition metal oxide
(Continued)

promoter in preparation of a catalyst containing silver, a transition metal oxide promoter and a carrier through a slurry process. The present invention provides a propylene direct oxidation reaction catalyst, which is a supported silver catalyst used for preparing a propylene oxide from the propylene direct oxidation reaction, the catalyst including a molybdenum oxide and a tungsten oxide as a catalyst promoter.

17 Claims, 9 Drawing Sheets

(51) Int. Cl.

| | | |
|---|---|---|
| *C07D 301/36* | (2006.01) | |
| *B01J 37/03* | (2006.01) | |
| *B01J 35/00* | (2006.01) | |
| *C07D 303/04* | (2006.01) | |
| *B01J 21/06* | (2006.01) | |
| *B01J 23/28* | (2006.01) | |
| *B01J 23/30* | (2006.01) | |
| *B01J 35/10* | (2006.01) | |
| *B01J 37/00* | (2006.01) | |
| *B01J 37/04* | (2006.01) | |
| *B01J 37/08* | (2006.01) | |

(52) U.S. Cl.
CPC ......... *B01J 35/002* (2013.01); *B01J 35/1009* (2013.01); *B01J 35/1014* (2013.01); *B01J 35/1038* (2013.01); *B01J 37/0045* (2013.01); *B01J 37/031* (2013.01); *B01J 37/04* (2013.01); *B01J 37/08* (2013.01); *C07D 301/10* (2013.01); *C07D 301/36* (2013.01); *C07D 303/04* (2013.01); *Y02P 20/52* (2015.11)

(58) Field of Classification Search
CPC .... B01J 35/1014; B01J 35/1038; B01J 35/00; B01J 37/0045; B01J 37/04; B01J 37/08; B01J 37/00; C07D 301/10; C07D 301/36; C07D 303/04; Y02P 20/52
USPC .......................................................... 549/536
See application file for complete search history.

(56) References Cited

U.S. PATENT DOCUMENTS

| | | | |
|---|---|---|---|
| 5,221,795 A | 6/1993 | Clerici et al. | |
| 6,043,400 A | 3/2000 | Jorge | |
| 6,500,969 B1 * | 12/2002 | Zhou | ..................... C01B 15/029 549/518 |

FOREIGN PATENT DOCUMENTS

| | | |
|---|---|---|
| KR | 2001-0012888 A | 2/2001 |
| KR | 10-0476081 | 12/2005 |
| KR | 10-2009-0028719 A | 3/2009 |

OTHER PUBLICATIONS

Jin, Guojie et al.; "Direct epoxidation of propylene with molecular oxygen over Ag—$MoO_3$/$ZrO_2$ catalyst"; Catal. Today; vol. 93-95; 2004; pp. 173-182.
Jin, Guojie et al.; "Epoxidation of propylene by molecular oxygen over modified Ag—$MoO_3$ catalyst"; Catal. Lett.; vol. 87; Nos. 3-4; Apr. 2003; pp. 249-252.
Jin, Guojie et al.; "Modification of Ag—$MoO_3$/$ZrO_2$ catalyst with metallic chloride for propylene epoxidation by molecular oxygen"; Catal. Lett.; vol. 97; Nos. 3-4; Sep. 2004; pp. 191-192.
Lee, Eo Jin et al.; "Direct epoxidation of propylene to propylene oxide with molecular oxygen over Ag—Mo—W/$ZrO_2$ catalysts"; Catalysis Communications; 89; 2017; pp. 156-160.
Lu, Guanzhong et al.; "Epoxidation of propylene by air over modified silver catalyst"; Catal. Lett.; vol. 58; 1999; pp. 67-70.
Luo, Mengfei et al.; "Epoxidation of propylene over Ag—CuCl catalysts using air as the oxidant"; Catal. Lett.; vol. 86; Nos. 1-3; Mar. 2003; pp. 43-49.
Tullo, Alexander H.; "DOW, BASF to Build Propylene Oxide: Companies mark success in process with plans for plant in Belgium"; Chem. Eng. News; vol. 82; Issue 36; Sep. 6, 2004; 6pp.
Xi, Zuwei et al.; "Reaction-Controlled Phase-Transfer Catalysis for Propylene Epoxidation to Propylene Oxide"; Science; vol. 292; May 11, 2001; pp. 1139-1141.
Yao, Wei et al.; "Promotional effect of $Y_2O_3$ on the performance of Ag/α-$Al_2O_3$ catalyst for epoxidation of propylene with molecular oxygen"; J. Mol. Catal. A: Chem.; vol. 276; 2007; pp. 162-167.

* cited by examiner

PROPYLENE DIRECT OXIDATION REACTION CATALYST, METHOD FOR PREPARING SAME, AND METHOD FOR PREPARING PROPYLENE OXIDE THROUGH PROPYLENE DIRECT OXIDATION REACTION USING SAME

CROSS-REFERENCE TO RELATED APPLICATIONS

This application is a National Phase Patent Application and claims priority to and the benefit of International Application Number PCT/KR2017/009147, filed on Aug. 22, 2017, which claims priority to and the benefit of Korean Patent Application No. 10-2016-0106152, filed on Aug. 22, 2016, in the Korean Intellectual Property Office, the disclosure of each of which is incorporated herein in its entirety by reference.

TECHNICAL FIELD

The present invention relates to a propylene direct oxidation reaction catalyst, a method for preparing the same, and a method for preparing a propylene oxide through propylene direct oxidation reaction using the same, and more specifically to a catalyst having an improved yield in preparation of a propylene oxide from propylene and oxygen, a method for preparing the same, and a method for preparing a propylene oxide through propylene direct oxidation reaction using the same.

BACKGROUND ART

Propylene oxide is a colorless and highly reactive material having a molecular formula of $CH_3CHCH_2O$. Since the propylene oxide is a volatile, low boiling point, and flammable liquid in terms of chemical properties, the propylene oxide is likely to be exploded by heat or flame and is thus very dangerous. Also, the propylene oxide has the feature of being well mixed with water and most organic solvents, and reacting vigorously with hydrogen chloride, chlorosulfonic acid, and hydrogen fluoride. The propylene oxide is most widely used as a raw material for synthesis of polyether polyol. In addition, the propylene oxide is used in various fields as a raw material for propylene glycol (PG), glycol ethers, butanediol, surfactants, starch and the like. In particular, with growth of markets for polyurethane and propylene glycol using polyol as a raw material, demand for the propylene oxide is also expected to increase steadily by 3-4% per year. Considering factors such as an increase in propylene cost due to an increase in oil price since the 2000s, it is expected that the importance of propylene oxide becomes higher and higher.

Most of propylene oxides so far have been prepared by a chlorohydrin process (see Patent Document 1) using chlorine as a raw material through propylene indirect oxidation, and a hydroperoxide process using an organic peroxide as a raw material (see Patent documents 2 and 3). However, the propylene indirect oxidation is a disadvantageous in that byproducts are necessary to be separated, refined and recycled, in addition to environmental problems or in that ensuring of sales lines is necessary.

Therefore, a novel process for improving the occurrence of byproducts, which is a disadvantage of the commercialization process, and for preparing an environmental-friendly propylene oxide has been developed. Although a HPPO process (see Patent Document 4 and Non-Patent Document 1), in which the propylene oxide was synthesized by oxidizing propylene by using hydrogen peroxide as a raw material, and only water was produced as a byproduct, was developed by Dow, BASF and Degussa, there was a limitation in preparing a large amount of propylene oxide due to a high cost of hydrogen peroxide used as a reactant.

In all of the above-described processes, the propylene oxide is synthesized by using a reactant other than oxygen. This provides an advantage of a high yield, but leads to a disadvantage that the reactant is expensive and additionally produced byproducts should be processed. Therefore, the necessity of a process for preparing a propylene oxide through a direct oxidation reaction between propylene and oxygen without using additional reactants is emerging.

Since only propylene and oxygen are used as raw materials in the process for preparing the propylene oxide through propylene direct oxidation, this process is advantageous in that the raw materials may be easily supplied and received, and the propylene oxide may be synthesized without producing additional byproducts. However, it is difficult to obtain the propylene oxide at a high yield due to a very low conversion rate and selectivity, so that there is no commercialization process. It has been known that this is because the complete oxidation reaction in which water and carbon dioxide are produced during the oxidation reaction of propylene is thermodynamically more stable than the partial oxidation reaction in which propylene oxide is produced. Thus, the complete oxidation reaction occurs in most cases in the absence of catalyst during the reaction between propylene and oxygen, so that it is disadvantageous in preparation of propylene oxide.

In general, as a catalyst for propylene direct oxidation reaction, studies have been conducted to improve the performance of a catalyst used for preparing an ethylene oxide through a reaction between ethylene and vapor-phase oxygen (see Non-Patent Document 2). However, it has been known that commercially feasible results cannot be obtained when this catalyst is applied to the propylene direct oxidation reaction by using catalysts and reaction conditions for ethylene direct oxidation reaction, which is currently commercialized, Therefore, studies on a particular catalyst for propylene direct oxidation have been conducted.

First, a silver catalyst prepared through a precipitation method by introducing various kinds of alkaline (earth) metal halides (NaCl, $BaCl_2$, LiCl, and $NH_4Cl$) without a support exhibits a propylene conversion rate of 14% and a propylene oxide selectivity of 15-35% (see Non-Patent Document 3). However, improved effects are not visibly shown in an aspect of the reaction activity, and it can be said that it is disadvantageous in that silver is used at a very high proportion of 95% by weight in the prepared catalyst. In addition, it is observed that a silver-copper chloride (Ag—CuCl) catalyst (see Non-Patent Document 4), in which copper chloride (CuCl) is introduced as a co-catalyst, had a possibility of preparation for propylene oxide; however, there is a limitation that improved effects is not greatly achieved in an aspect of the reaction activity.

On the other hand, it is observed that a silver catalyst in which a chloride salt and a molybdenum oxide are introduced as a promoter without a support exhibits a propylene conversion rate of 6.8% and a propylene oxide selectivity of 53% (see Non-Patent Document 5). It can be said that this study is excellent in that an experiment was conducted without additional promoting gas and it is reported that molybdenum oxide exhibits an effect as a promoter in addition to chloride salts or alkaline (earth) metals which have been studied in other researches. However, it can be said that the above catalyst still has a disadvantage in that expensive molybdenum and silver were respectively used in a large amount, e.g., 50 wt %, in the prepared catalyst.

Therefore, studies for introducing various supports have been conducted in order to improve the yield of propylene oxide and to minimize the amount of silver, which is an active metal, in the preparation of catalysts.

A silver catalyst prepared by adding a potassium salt promoter to an alkaline earth metal carbonate support exhibits a propylene conversion rate of 34% and a propylene oxide selectivity of 47% in a propylene direct oxidation reaction, resulting in improved reaction activity (see Patent Document 5). However, a relatively expensive silver (40 wt %) is still used in this study, and this catalyst is not favorable economically because additional organic chloride promoting gas is added during the reaction.

A silver catalyst, in which a metal chloride salt and a molybdenum oxide are introduced as a promoter to a zirconium oxide support exhibits a propylene conversion rate of 2.0% and a propylene oxide selectivity of 65.0% (see Non-Patent Document 6). In this study, a relatively low proportion (20 wt %) of silver is used unlike other studies, and it is reported that this catalyst is improved in terms of propylene oxide selectivity. However, a conversion rate is low as compared to a high selectivity, so that it is disadvantageous in terms the yield of propylene oxide.

In addition, there are a silver catalyst prepared by adding an $Y_2O_3$ promoter to an $\alpha$-$Al_2O_3$ support (see Non-Patent Document 7), a silver catalyst prepared by adding a $MoO_3$ promoter to a $ZrO_2$ support (see Non-Patent Document 8), etc. All of these catalysts are composed of a low amount of silver compared with the catalysts prepared without the conventional support, but still have a disadvantage in terms of the selectivity and yield of propylene oxide. Thus, it is necessary to study the effect of the support on the propylene direct oxidation.

Meanwhile, it is important to understand a partial oxidation mechanism in the silver catalyst for the effective conversion of propylene oxide through the propylene direct oxidation reaction (see Non-Patent Document 9). In order to produce propylene oxide in this reaction, the oxygen adsorbed at an active site of silver should react with carbon located at a double bond of propylene, which is a reactant, to cause a partial oxidation reaction. However, it is known that since the reactivity of the allylic hydrogen present at a methyl group of propylene is very high, the complete oxidation reaction, in which carbon dioxide and water are generated through the reaction between oxygen adsorbed at silver and allylic hydrogen, dominantly occurs and thus the propylene oxide is not effectively produced. Therefore, when the oxygen adsorbed at the silver is not reacted with allylic hydrogen present at the methyl group of propylene but selectively reacted with carbon located at the double bond of propylene, a high yield of propylene oxide may be expected.

PRIOR ART DOCUMENTS

Patent Document 1: U.S. Pat. No. 6,043,400
Patent Document 2: U.S. Pat. No. 3,439,001
Patent Document 3: U.S. Pat. No. 5,210,354
Patent Document 4: U.S. Pat. No. 5,221,795
Patent Document 5: Canada Patent No. 1282772
Non-Patent Document 1: A. Tullo, Chem. Eng. News, vol. 82, p. 15 (2004)
Non-Patent Document 2: Z. W. Xi, N. Zhou, Y. Sun, K. L. Li, Science, vol. 292, p. 1139 (2001)
Non-Patent Document 3: G. Lu, X. Zuo, Catal. Lett., Vol. 48, p. 67 (1997)
Non-Patent Document 4: M. Luo, J. Lu, C. Li, Catal. Lett., vol. 86, p. 1 (2003).
Non-Patent Document 5: G. Jin, G. Lu, Y. Guo, J. Wang, X. Liu, Catal. Lett., Vol. 87, p. 3 (2003)
Non-Patent Document 6: G. Jin, G. Lu, Y. Guo, Y. Guo, J. Wang, X. Liu, W. Kong, X. Liu, Catal. Lett., Vol. 97, p. 3 (2004)
Non-Patent Document 7: W. Yao, G. Lu, Y. Guo, Y. Wang, Z. Zhang, J. Mol. Catal. A, vol. 276, p. 162 (2007).
Non-Patent Document 8: G. Jin, G. Lu, Y. Guo, J. Wang, X. Liu, Catal. Today, vol. 93, p. 173 (2004).
Non-Patent Document 9: Z. M. Hu, H. Nakai, H. Nakatsuji, Surf. Sci., Vol. 401, p. 371 (1998)

DISCLOSURE OF THE INVENTION

Technical Problem

The present invention is directed to providing a propylene direct oxidation reaction catalyst capable of preparing a propylene oxide from propylene and oxygen at a higher yield than the case of using conventionally prepared catalysts by adopting a specific transition metal oxide promoter in preparing a catalyst containing silver, a transition metal oxide promoter and a carrier through a slurry process.

In addition, the present invention is directed to providing a propylene direct oxidation reaction catalyst preparing method capable of preparing a catalyst having a higher yield than conventionally prepared catalysts.

Furthermore, the present invention is directed to providing a method capable of preparing a propylene oxide with an improved yield by using the catalyst, in which propylene oxide selectivity is increased while maintaining a predetermined level of propylene conversion rate.

Furthermore, the present invention is directed to providing a method for producing a zirconium oxide support (carrier) by carrying a metal oxide composed of silver-transition metal oxide, the method being capable of obtaining high activity even when applied to a propylene direct oxidation reaction.

Technical Solution

The present invention is directed to solving the above described problems, there is provided a propylene direct oxidation reaction catalyst, which is a supported silver catalyst used for preparing a propylene oxide from a propylene direct oxidation reaction, the catalyst including, as a catalyst promoter, a molybdenum oxide ($MoO_3$) and a tungsten oxide ($WO_3$).

Also, the silver is included in an amount of 5-30% by weight with respect to the entire catalyst.

Also, the promoter is included in an amount of 1-20% by weight with respect to the entire catalyst.

Also, the molybdenum oxide to the tungsten oxide is included, by weight percentage, at a ratio of 1:99 to 99:1.

Also, a carrier used for the support is a zirconium oxide.

Also, the zirconium oxide is prepared according to a method including the steps of:
(i) dissolving a zirconium oxide precursor in a solvent to prepare a zirconium oxide precursor solution;
(ii) adding a basic aqueous solution to the zirconium oxide precursor solution;
(iii) stirring the solution prepared in the step (ii) and then filtering to obtain a solid precipitate; and (iv) drying the solid precipitate to obtain a solid material.

Also, the zirconium oxide precursor is at least one selected from the group consisting of a nitrate-based precursor, a chloride-based precursor, a bromide-based precursor, an acetate-based precursor, and an acetylacetonate-based precursor.

Also, the zirconium oxide has a monoclinic crystal phase fraction of 0.15-1.00 as calculated based on X-ray diffraction analysis results according to the following equation:

Monoclinic crystal phase peak height/(monoclinic crystal phase peak height+tetragonal crystal phase peak height)                    (Equation).

Another aspect of the present invention is directed to solving the above-described problems, there is provided a method for preparing a propylene direct oxidation reaction catalyst, the method including: (a) dissolving a silver precursor in a solvent to prepare a silver precursor solution; (b) dissolving, in the silver precursor solution, a molybdenum oxide precursor and a tungsten oxide precursor as a metal oxide precursor to prepare a silver-metal oxide precursor solution; (c) adding a zirconium oxide to the silver-metal oxide precursor solution to prepare a silver-metal oxide precursor/zirconium oxide slurry; and (d) stirring the slurry, then drying the slurry and heat treating the obtained solid material to prepare a catalyst.

Also, the solvent is a mixed aqueous solution of water and at least one organic solvent selected from the group consisting of amines, acids and glycols.

Also, the silver precursor is at least one selected from the group consisting of silver oxide, silver nitrate, silver carbonate, silver acetate, silver oxalate, silver lactate, silver citrate and silver propionate.

Also, the molybdenum oxide precursor and the tungsten oxide precursor are each independently at least one selected from the group consisting of a nitrate-based precursor, a chloride-based precursor, an acetate-based precursor, and an ammonium-based precursor.

Also, the zirconium oxide is prepared according to a method including the steps of:
(i) dissolving a zirconium oxide precursor in a solvent to prepare a zirconium oxide precursor solution;
(ii) adding a basic aqueous solution to the zirconium oxide precursor solution;
(iii) stirring the solution prepared in the step (ii) and then filtering to obtain a solid precipitate; and
(iv) drying the solid precipitate to obtain a solid material.

Also, the solvent is any one selected from the group consisting of water, an alcohol having 1-4 carbon atoms, and a mixture thereof.

Also, the step (ii) includes adding a basic aqueous solution to adjust the pH of the zirconium oxide precursor solution to 3 to 14.

Also, the heat treatment is performed at 100-600° C. for 1-8 hours.

Another aspect of the present invention is directed to solving the above described problems, there is provided a method for a propylene oxide through a propylene direct oxidation reaction catalyst in the presence of the above-described catalyst.

Also, the direct oxidation of propylene is performed under conditions in which: among total raw materials, the propylene is contained in an amount of 10-50 vol %, oxygen is contained in an amount of 5-25 vol % and inert gas is contained in an amount of 25-85 vol %; and a gas hourly space velocity (GHSV) is 1,000-20,000 $h^{-1}$.

Also, the propylene direct oxidation reaction is performed at a temperature of 300-600° C. under a pressure of atmospheric pressure to 50 atm.

Advantageous Effects

The present invention provides an effective alternative capable of easily preparing a propylene oxide from propylene, demands and values of which are gradually increasing globally, and is advantageous in that it is possible to prepare a propylene oxide directly from propylene without using any additional reactant other than oxygen to thereby achieve an economic benefit and also possible to actively cope with future market changes.

In addition, the catalyst according to the present invention has a dominant position in terms of economy by including a relatively low silver content as compared with catalysts prepared by conventional methods.

Furthermore, a method for preparing catalyst according to the present invention facilitates the preparation of a catalyst through a one-step process of a slurry method, and exhibits a high propylene oxide selectivity while maintaining a predetermined level of a propylene conversion rate, thereby enabling propylene oxide to be prepared with an improved yield.

MODE FOR CARRYING OUT THE INVENTION

Figure 1:
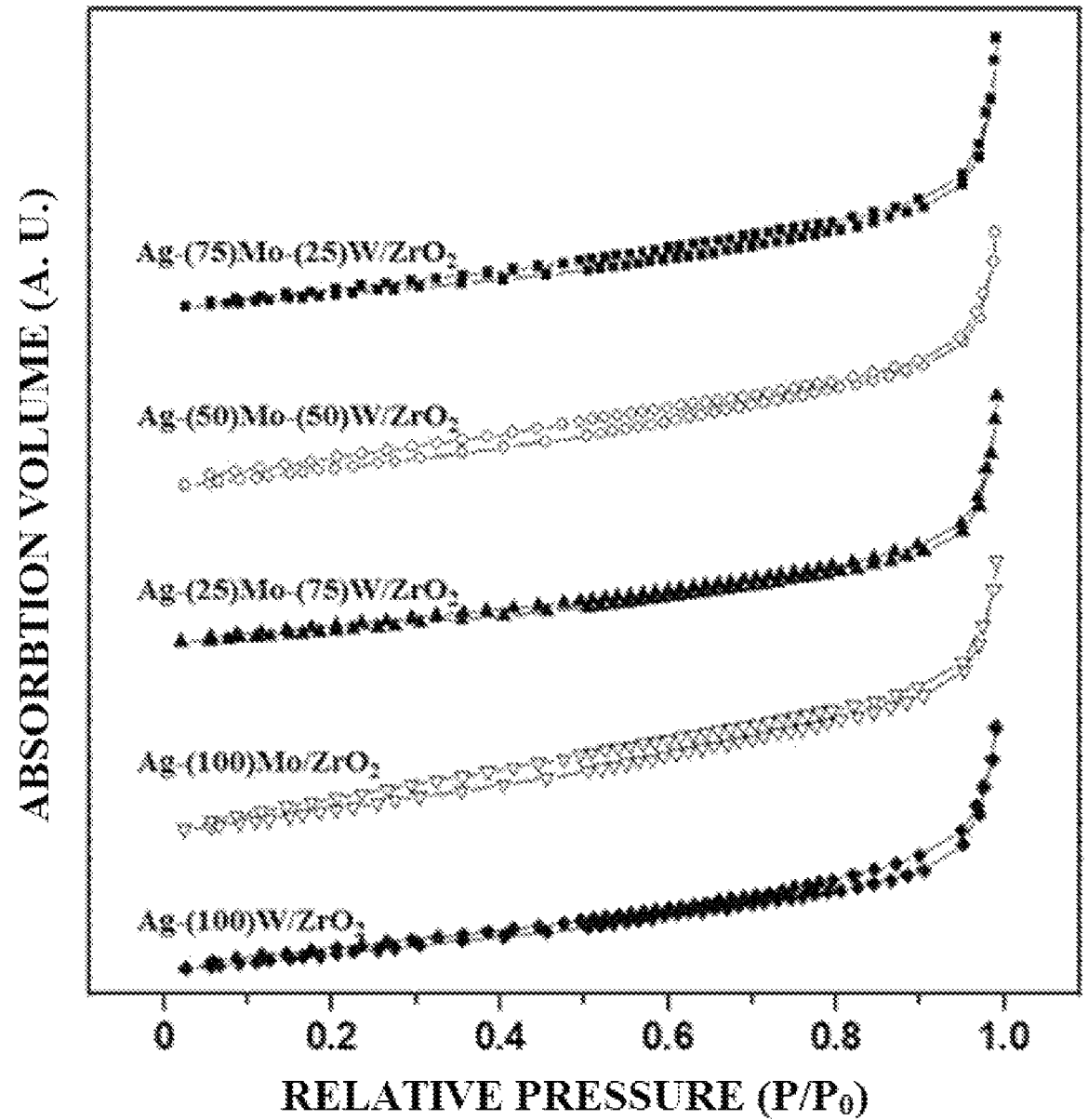
FIG. 1 is a graph showing results of nitrogen adsorption-desorption experiments on a catalyst prepared in Experimental Example 1 of the present invention.

Hereinafter, preferred embodiments of the present invention will be described in detail. In describing the present invention, when detailed description of the related known technology is deemed to blur the gist of the present invention, the detailed description will be omitted. Throughout the specification, when a part is referred to as "including" an element, it means that the part may include other elements as well without excluding the other elements unless specifically stated otherwise.

As a result of continuous research to improve the low activity of a supported silver catalyst used for preparing a propylene oxide from a propylene direct oxidation reaction, the present inventor has established a method for preparing a silver catalyst in which a molybdenum oxide and a tungsten oxide are simultaneously introduced as a promoter into a zirconium oxide carrier. Also, the present inventor has found that: when a catalyst thus prepared is used, the propylene oxide may be surprisingly prepared at a higher yield than the case of using conventional catalysts; and when the zirconium oxide carrier is prepared through a precipitation process under specific reaction conditions, a catalyst using the zirconium oxide carrier enables the propylene oxide to be prepared at a higher yield. Finally, the present inventors have completed the present invention.

Therefore, as a supported silver catalyst used for preparing a propylene oxide from a propylene direct oxidation reaction, the present invention discloses a propylene direct oxidation reaction catalyst including a molybdenum oxide ($MoO_3$) and a tungsten oxide ($WO_3$) as a catalyst promoter.

In the present invention, the silver, which is an active material, is included in an amount of 5 to 30% by weight in a total catalyst composition, and is included in a relatively low content as compared to conventional catalysts, and preferably the silver is included in an amount of 10 to 25% by weight. This is due to use of specific combination of catalyst promoters to be described later.

The propylene direct oxidation reaction catalyst according to the present invention includes a molybdenum oxide and a tungsten oxide as a catalyst promoter composed of a specific metal oxide. It is expected that the catalyst promoter composed of the molybdenum oxide and tungsten oxide does not react oxygen adsorbed at the silver with allylic hydrogen existing at a methyl group of propylene during a catalytic reaction process through propylene direct oxidation, and serves to promote the possibility of selectively reacting the oxygen with carbon positioned at a double bond of propylene.

The catalyst promoter according to the present invention is composed of a combination of specific metal oxides, so that a higher yield may be achieved under the same conditions compared to the case where the catalyst promoter is composed of at least the molybdenum oxide or the tungsten oxide alone.

The content of the catalyst promoter may be determined in consideration of the content of the active metal. With respect to the entire catalyst, the content of the catalyst promoter may be preferably 1 to 20% by weight, and more preferably, 2 to 10% by weight. When the content of the catalyst promoter is less than 1% by weight, it is difficult to expect a catalyst promotion effect. When the content of the catalyst promoter is more than 20% by weight, the degree of increase in the catalytic activity relative to the content may not be large.

Here, when the molybdenum oxide and tungsten oxide are simultaneously used, by wt %, in 1:99 to 99:1 in a catalyst promoter composition according to the present invention, it is confirmed that the preparation yield of propylene oxide through the propylene direct oxidation reaction is higher than that when the molybdenum oxide or the tungsten oxide is used alone; however, there is an optimal content ratio between the molybdenum oxide and tungsten oxide for maximizing the preparation yield of propylene oxide. That is, in the entire catalyst promoter, it is preferable to form the molybdenum oxide in a proportion of 30 to 90% by weight and the tungsten oxide in a proportion of 10 to 70% by weight, more preferable to form the molybdenum oxide in a proportion of 50 to 85% by weight and the tungsten oxide in a proportion of 15 to 50% by weight, most preferable to form the molybdenum oxide in a proportion of 70 to 80% by weight and the tungsten oxide in a proportion of 20 to 30% by weight. Although the yield tends to increase when a molybdenum oxide content is relatively high; however, when the molybdenum oxide content exceeds a predetermined level, that is, excessive, the yield is rather reduced.

In the present invention, zirconium oxide may be preferably used as a carrier used for the silver catalyst support. Although a previously known alkaline earth metal carbonate such as calcium carbonate may also be used as the carrier, it was confirmed in the present invention that the zirconium oxide is most suitable as a carrier in simultaneously carrying the molybdenum oxide and tungsten oxide as a catalyst promoter together with an active metal. Most preferably, the zirconium oxide used for the silver catalyst support may be prepared according to a method including a specific step, and details therefor will be described later.

Furthermore, the zirconium oxide has a monoclinic crystal phase at a ratio of 0.15-1.00 as calculated based on X-ray diffraction analysis results according to the following equation:

Monoclinic crystal phase peak height/(monoclinic crystal phase peak height+tetragonal crystal phase peak height)  (Equation).

The zirconium oxide may have a monoclinic crystal phase fraction of preferably 0.30 to 0.99, more preferably 0.50 to 0.97, even more preferably 0.70 to 0.95, and most preferably 0.85 to 0.95.

The catalyst according to the present invention may be easily prepared in a one-step process of a slurry method.

Therefore, another aspect of the present invention discloses a method for preparing a propylene direct oxidation reaction catalyst, the method including the steps of: (a) dissolving a silver precursor in a solvent to prepare a silver precursor solution; (b) dissolving a molybdenum oxide precursor and a tungsten oxide precursor as a metal oxide precursor in the silver precursor solution to prepare a silver-metal oxide precursor solution; (c) adding a zirconium oxide to the silver-metal oxide precursor solution to prepare a silver-metal oxide precursor/zirconium oxide slurry; and (d) stirring the slurry, then drying the slurry, and heat treating the obtained solid material thereby preparing a catalyst.

The solvent used to prepare the silver precursor solution in step (a) should be capable of dissolving the silver precursor appropriately or converting the silver precursor into a soluble form and also be capable of being easily removable by subsequent a washing, volatilization or oxidation process. In addition, it is generally preferred that the solvent is easily mixed with water since an aqueous solution may be used conveniently. Therefore, the solvent suitable for preparing the silver precursor solution is a mixed aqueous solution of water and organic substances such as amines, acids, and glycols.

The amines may include, for example, triethanolamine, ethylenediamine, triethylamine, ethanolamine and the like; the acids may include, for example, citric acid, malonic acid, propionic acid, oxalic acid, lactic acid, and the like; and the glycols may include, for example, ethylene glycol, triethylene glycol, propylene glycol and the like.

The silver precursor used for forming the silver precursor solution in the solvent is not particularly limited, and thus any silver compound known in the art, which is soluble in the solvent, does not have a reactivity therebetween, and is able to be converted to metallic silver, may also be used. Such a silver precursor may include, for example, silver oxide, silver nitrate, silver carbonate, silver acetate, silver oxalate, silver lactate, silver citrate, silver propionate and the like, and preferably, the silver oxide, which is easily reduced to a metallic form under calcination conditions, may be used.

The step (b) may include preparing a silver-metal oxide precursor solution by adding a metal oxide as a catalyst promoter, and the metal oxide may have a liquid or solid form to be applied to the prepared silver precursor solution. That is, this is the case the metal oxide that is soluble in the same solvent used to form the silver precursor solution, and in the present invention, the molybdenum oxide precursor and the tungsten oxide precursor are dissolved in the silver precursor solution to prepare the silver-metal oxide precursor solution.

In the present invention, the molybdenum oxide precursor and the tungsten oxide precursor are not particularly limited, and may thus be selected and used from among a nitrate-based precursor, a chloride-based precursor, an acetate-based precursor, an ammonium-based precursor, and the like. Preferably, an ammonium-based precursor may be used.

The step (c) may include dissolving a carrier material in the prepared silver-metal oxide precursor solution to produce a slurry. In the present invention, a silver-metal oxide precursor/zirconium oxide slurry is prepared by selecting a zirconium oxide as a support and adding the zirconium oxide to the silver-metal oxide precursor solution.

In the present invention, very high propylene oxide selectivity of the zirconium oxide may be achieved by simultaneously carrying the molybdenum oxide and tungsten oxide used as a catalyst promoter together with silver that is an active metal.

Preferably, the zirconium oxide may be prepared according to a method including the steps of:
(i) dissolving a zirconium oxide precursor in a solvent to prepare a zirconium oxide precursor solution;
(ii) adding a basic aqueous solution to the zirconium oxide precursor solution;
(iii) stirring the solution prepared in the step (ii) and then filtering to obtain a solid precipitate; and
(iv) drying the solid precipitate to obtain a solid material.

The zirconium oxide precursor used in the step (i) is typically used in the art, and is not particularly limited. Thus, at least one selected from the group consisting of a nitrate-based precursor, a chloride-based precursor, a bromide-based precursor, an acetate-based precursor and an acetylacetonate-based precursor may be used as zirconium oxide precursor, and nitrate-based may be preferably used.

The solvent used in step (i) may employ any one selected from the group consisting of water, an alcohol having 1-4 carbon atoms, and a liquid mixture thereof, and may preferably employ water.

With respect to the zirconium oxide precursor, the solvent may be used in 10-100 ml/zirconium oxide precursor mass (g), preferably, 20-80 ml/zirconium oxide precursor mass (g), more preferably, 30 70 ml/zirconium oxide precursor mass (g), and most preferably, 40-60 ml/zirconium oxide precursor mass (g). Since an amount of the solvent used, which is equal to or less than 10 ml/zirconium oxide precursor mass (g), is not enough to disperse the zirconium oxide precursor, it is preferable to maintain the above-described amount.

The kind of the basic aqueous solution used in the step (ii) is not particularly limited. Thus, the basic aqueous solution may employ preferably at least one selected from the group consisting of aqueous ammonia solution, aqueous potassium hydroxide solution and aqueous sodium hydroxide solution may be used, and may employ more preferably an aqueous ammonia solution.

The basic aqueous solution used in the step (ii) may use an aqueous solution having a weight percentage of 25 to 30% with respect to water, and preferably use 28-30 wt& of an aqueous ammonia solution. It is preferable that the basic aqueous solution is introduced until the pH of the zirconium oxide precursor solution is 3 to 14 to thereby form a monoclinic crystal phase of zirconium. The basic aqueous solution may be more introduced preferably until the pH of the zirconium oxide precursor solution is 5 to 13, even more preferably until the pH is 6 to 12, and most preferably until the pH is 8 to 12.

The stirring of the support forming solution prepared in the step (iii) may be performed at a temperature of 10-50° C. at a speed of 1000-10000 rpm for 1-24 hours, and preferably at a temperature of 20-35° C. and at a speed of 4000-7000 rpm for 3-8 hours to obtain the solid precipitate.

The solid martial obtained by filtration after the step (iii) is washed with distilled water to remove the remaining aqueous ammonia solution, and washing with C1-C4 alcohol may be further included in order to prevent a shrinkage phenomenon during drying.

The drying in the step (iv) may be performed at a temperature of 70-150° C. for 12 hours or more. The solvent, remaining aqueous ammonia solution, impurities and the like are removed by such drying.

After the step (iv), the grinding and calcinating of the solid material obtained in the step (iv) may be further performed. The calcinating may be performed at a temperature of 400-1000° C. for 3-12 hours. The zirconium oxide support is formed from the zirconium oxide precursor through the calcinating. When the calcinating temperature and the calcinating time are respectively fall within the above ranges, not only a nitrate group and an ammonium hydroxyl group, which remain in the zirconium oxide support, may be completely removed but also high catalytic activity may be maintained.

In the present invention, the prepared zirconium oxide according to the above method may have a monoclinic crystal phase fraction of 0.15-1.00, as calculated based on X-ray diffraction analysis results according to the following equation:

$$\text{Monoclinic crystal phase peak height/(monoclinic crystal phase peak height+tetragonal crystal phase peak height)} \quad \text{(Equation)}.$$

The zirconium oxide may have a monoclinic crystal phase fraction of preferably 0.30-0.99, more preferably 0.50-0.97, even more preferably 0.70-0.95, and most preferably 0.85-0.95.

Thereafter, the prepared slurry is stirred and dried as in the step (d) to obtain a solid material, the obtained solid material is heat-treated to remove volatile components, so that the silver compound is reduced to an elemental form to thereby prepare a silver-molybdenum oxide-tungsten oxide/zirconium oxide catalyst.

Here, the drying and heat treatment may be preferably performed such that the drying process is performed at 50-200° C. for 3-36 hours and then the heat treatment process may be performed at 100-600° C. for 1-8 hours. More preferably, the drying process is performed at 100-140° C. for 18-30 hours, and then heat treatment process may be performed at 400-500° C. for 2-5 hours.

Meanwhile, it is needless to say that other commonly used activators, accelerators, reinforcement agents, stabilizers, improvement agents, or the like in addition to the components set forth in the present invention may also be used within typical content ranges.

The above-described catalyst according to the present invention is used for propylene direct oxidation reaction.

Therefore, another aspect of the present invention discloses a method for preparing a propylene oxide through propylene direct oxidation reaction in the presence of the prepared catalyst.

A propylene and an oxygen-containing gas in the propylene direct oxidation reaction are introduced into a reactor in the presence of the prepared catalyst under process conditions effective to achieve minimum partial oxidation of propylene into the corresponding oxide thereof. The oxygen used in the reaction may be derived from pure molecular oxygen, atomic oxygen, atomic or molecular oxygen, be a transient radical species that may be present under the oxidation reaction conditions, and may be a mixture of at least one of the oxygens above and another gaseous substance. Typically, the oxygen may be introduced into the reactor as air, commercially available pure oxygen, or other materials that are in a gaseous state and form molecular oxygen under oxidation reaction conditions.

In the case of raw materials to be introduced into the reactor, it is preferable that, in the total raw materials (feed stream), propylene may be in a range of 10-50% by volume, the oxygen may be in a range of 5-25% by volume and inert gas may be in a range of 25-85% by volume, and gas hourly space velocity (GHSV) that is total gas flow/catalyst volume may be performed under a condition of 1,000-20,000 h$^{-1}$; and it is more preferable that the propylene may be in a range of 15-25% by volume, the oxygen may be in a range of 5-15% by volume, and a GHSV may be performed under a condition of 2,000-5,000 h$^{-1}$. In addition, the process may be performed at a reaction temperature of 300-600° C. under a pressure of atmospheric pressure to 50 atm, preferably at a reaction temperature of 350-550° C. under a pressure of atmospheric pressure to 30 atm, even more preferably at a reaction temperature of 400-500° C. under a pressure of an atmospheric pressure to a pressure of 20 atm, most preferably at a reaction temperature of 450-500° C. under a pressure of atmospheric pressure to 10 atm.

Furthermore, the feed stream may include a ballast or diluent, e.g., nitrogen or other inert gas, especially, in the case of using air as an oxygen source. The feed stream may also include water vapor partially in addition the above.

Hereinafter, the present invention will be described in more detail with reference to examples.

Example 1

A catalyst was prepared by using a slurry method as follows. 6 ml of distilled water, 0.9 ml of ethylenediamine and 1.63 g of oxalic acid were put into a beaker, and then 1 g of oxide ($Ag_2O$) was input and mixed. Then, after a silver precursor was completely dissolved, 0.1725 g of ammonium molybdate (($NH_4$)$_2MoO_4$) and 0.0575 g of ammonium (para)tungstate (($NH_4$) $10H_2(W_2O_7)_6$-$xH_2O$) were introduced into a solvent in which the silver precursor was dissolved such that a weight ratio of the sum of a molybdenum oxide ($MoO_3$) and a tungsten oxide ($WO_3$) to the total weight of the finally prepared catalyst was fixed to 5 wt %, and then a weight ratio of the molybdenum oxide to the tungsten oxide was 75:25. Thereafter, when 3.54 g of a zirconium oxide (Sigma-Aldrich) as a support material was introduced, a slurry material was obtained. When a slurry was stirred at 60° C. until moisture evaporates, a solid material remained. Then, the solid material was further dried in an oven at 120° C. for 24 hours. Then, the dried solid material was made into a powder form, heated to 460° C. in an air atmosphere at a rate of 5° C. per minute, and then maintained and calcinated for 3 hours to prepare a silver-molybdenum oxide-tungsten oxide/zirconium oxide catalyst (Ag—Mo-(25)W/$ZrO_2$).

Example 2

A catalyst (Ag-(50)Mo-(50)W/$ZrO_2$) was prepared in the same manner as in Example 1, except that the weight of the molybdenum oxide to the tungsten oxide in Example 1 was changed to 50:50%.

Example 3

A catalyst (Ag-(25)Mo-(75)W/$ZrO_2$) was prepared in the same manner as in Example 1, except that the weight of the molybdenum oxide to the tungsten oxide in Example 1 was changed to 25:75%.

Comparative Example 1

A catalyst (Ag-(100)Mo/$ZrO_2$) was prepared in the same manner as in Example 1, except that the weight of the molybdenum oxide to the tungsten oxide in Example 1 was changed to 100:0%.

Comparative Example 2

A catalyst (Ag-(100)W/$ZrO_2$) was prepared in the same manner as in Example 1, except that the weight of the molybdenum oxide to the tungsten oxide in Example 1 was changed to 0:100%.

Experimental Example 1

To investigate characteristics of silver-molybdenum oxide-tungsten oxide/zirconium oxide catalysts, nitrogen adsorption-desorption experiments, X-ray diffraction analysis and scanning electron microscopic image analysis were performed on catalysts prepared according to the above Examples and Comparative Examples. The results of the nitrogen adsorption-desorption experiments were shown in FIG. 1 and Table 1 below, the results of the X-ray diffraction analysis were shown in FIG. 2, and the results of the scanning electron microscopic image analysis were shown in FIG. 3.

TABLE 1

| Catalyst | Specific surface area (m$^2$/g) | Pore volume (cm$^3$/g) |
|---|---|---|
| Ag-(75)Mo-(25)W/$ZrO_2$ | 6.0 | 0.02 |
| Ag-(50)Mo-(50)W/$ZrO_2$ | 7.3 | 0.02 |
| Ag-(25)Mo-(75)W/$ZrO_2$ | 7.0 | 0.02 |
| Ag-(100)Mo/$ZrO_2$ | 8.3 | 0.02 |
| Ag-(100)W/$ZrO_2$ | 6.7 | 0.02 |

First, referring to FIG. 1, all of the prepared catalysts exhibit a type-II nitrogen adsorption-desorption isotherm, showing characteristics of a material in which typical pores are not present. It can be confirmed that the catalysts thus prepared were formed in a shape in which a pore structure was hardly developed.

In addition, referring to Table 1, the analysis results demonstrated that the prepared catalyst had a specific surface area of about 6.0 to 8.3 m²/g, and a pore volume was of about 0.02 cd/g. It can be confirmed that the catalyst was prepared well in a shape in which the pore structure was hardly developed.

Figure 2:
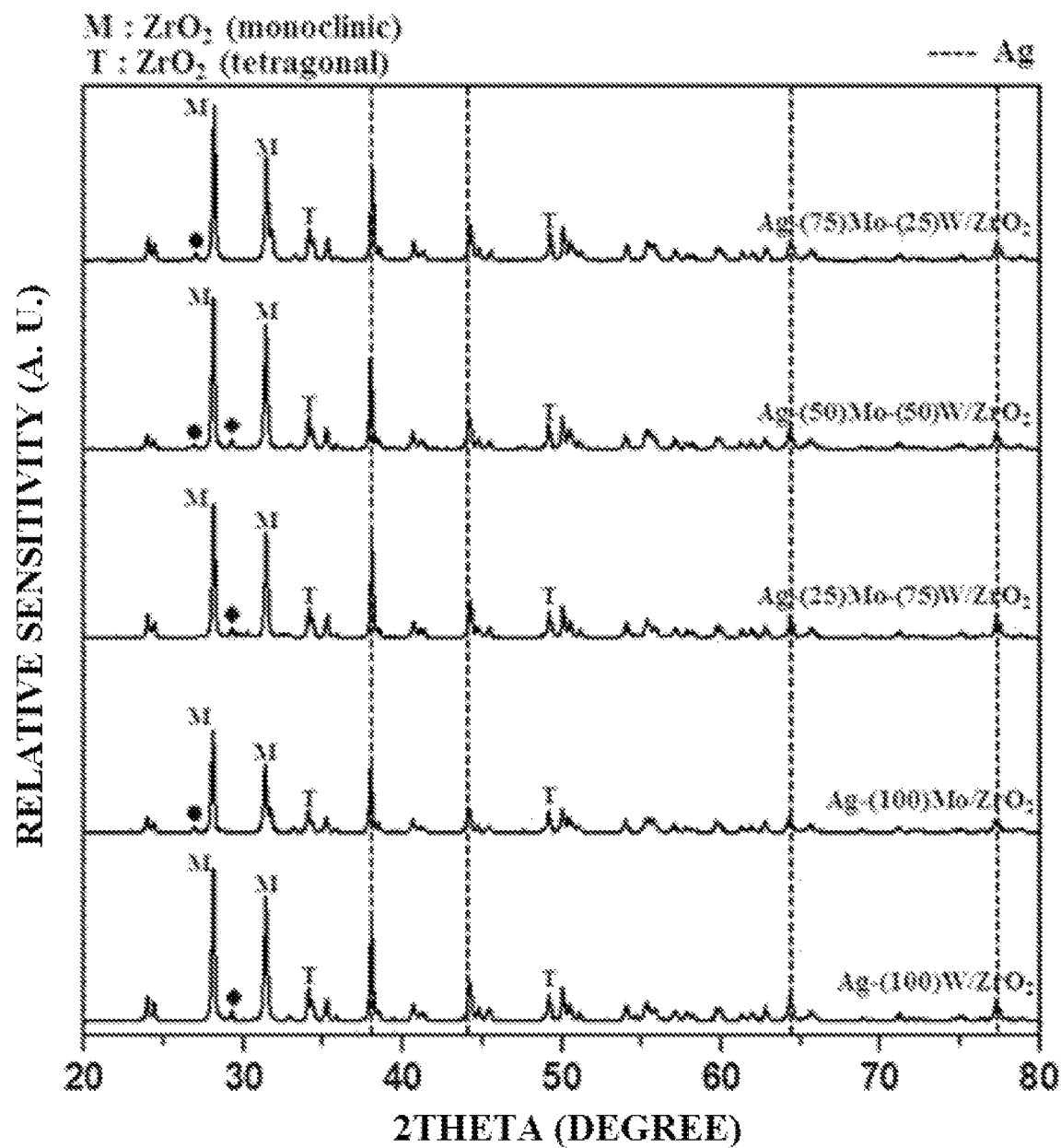
FIG. 2 is a graph showing results of X-ray diffraction analysis of a catalyst prepared in Experimental Example 1 of the present invention.

Then, referring to FIG. 2, it can be observed that all of the prepared catalysts exhibited silver's inherent metal peaks at around 2θ=38°, 44°, 64° and 77°, zirconium oxide monoclinic phase peaks at around 2θ=28° and 31°, and zirconium oxide tetragonal phase peaks at around 2θ=34° and 49°. Furthermore, a tungsten oxide-related peak appeared at 2θ=27° and a molybdenum oxide-related peak appeared at around 2θ=29°.

Figure 3:
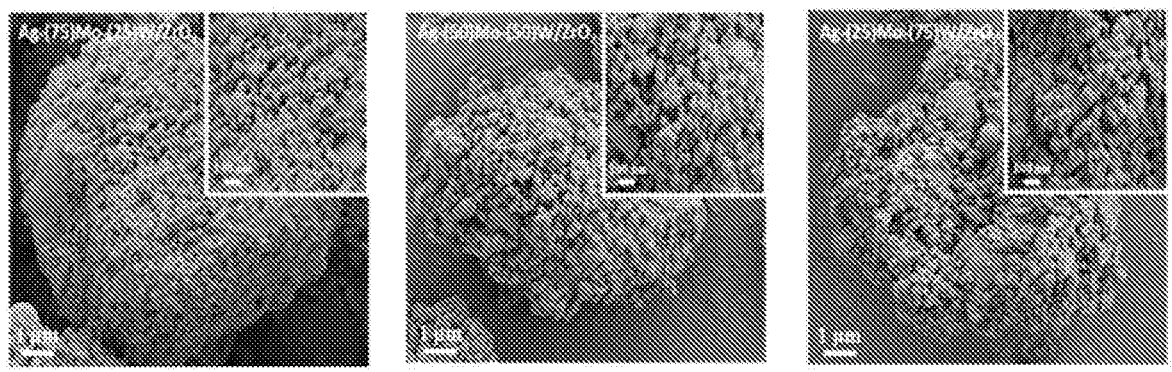
FIG. 3 is photographs showing results of scanning electron microscopic image analysis of a catalyst prepared in Experimental Example 1 of the present invention.

Afterwards, referring to FIG. 3, in the silver-molybdenum oxide-tungsten oxide/zirconium oxide catalyst according to the present invention, it can be confirmed that both the silver particles and the promoter particles are uniformly present on the zirconium oxide in such a shape that the pore structure of about 100-300 nm was scarcely developed.

Experimental Example 2

A propylene oxide preparation reaction was performed through propylene direct oxidation reaction using the catalysts prepared according to the above-described Examples and Comparative Examples. A feed stream consisting of 16.7 vol % of propylene, 8.3 vol % of oxygen, and 75.0 vol % of nitrogen, as a reactant composition, was made to pass through a catalyst layer of a quartz reactor, so that the propylene direct oxidation reaction was performed without additional promoting gases. At this point, the temperature of the reactor was 460° C. and the pressure thereof was atmospheric pressure. A total flow rate of the reactant with respect to the volume of the catalyst was maintained at 12,000 h⁻¹ (60 cc/min ($N_2+O_2+C_3H_6$), catalyst volume 0.3 cc). The propylene conversion rate, propylene oxide selectivity and propylene oxide yield were calculated by following Equations 1-3, respectively, and the results were shown in FIG. 4 and Table 2 below.

Propylene conversion rate (%)=(mass of consumed propylene/mass of supplied propylene)×100  [Equation 1]

Propylene oxide selectivity (%)=(mass of produced propylene oxide/mass of consumed propylene)×100  [Equation 2]

Propylene oxide yield (%)=(mass of produced propylene oxide/mass of supplied propylene)×100  [Equation 3]

TABLE 2

| Catalyst | Propylene conversion rate (%) | Propylene oxide selectivity (%) | Propylene oxide yield (%) |
|---|---|---|---|
| Ag-(75)Mo-(25)W/ZrO₂ | 11.5 | 58.1 | 6.68 |
| Ag-(50)Mo-(50)W/ZrO₂ | 9.3 | 50.6 | 4.71 |
| Ag-(25)Mo-(75)W/ZrO₂ | 8.7 | 44.1 | 3.8 |
| Ag-(100)Mo/ZrO₂ | 12.4 | 29.3 | 3.63 |
| Ag-(100)W/ZrO₂ | 5.9 | 15.4 | 0.9 |

Figure 4:
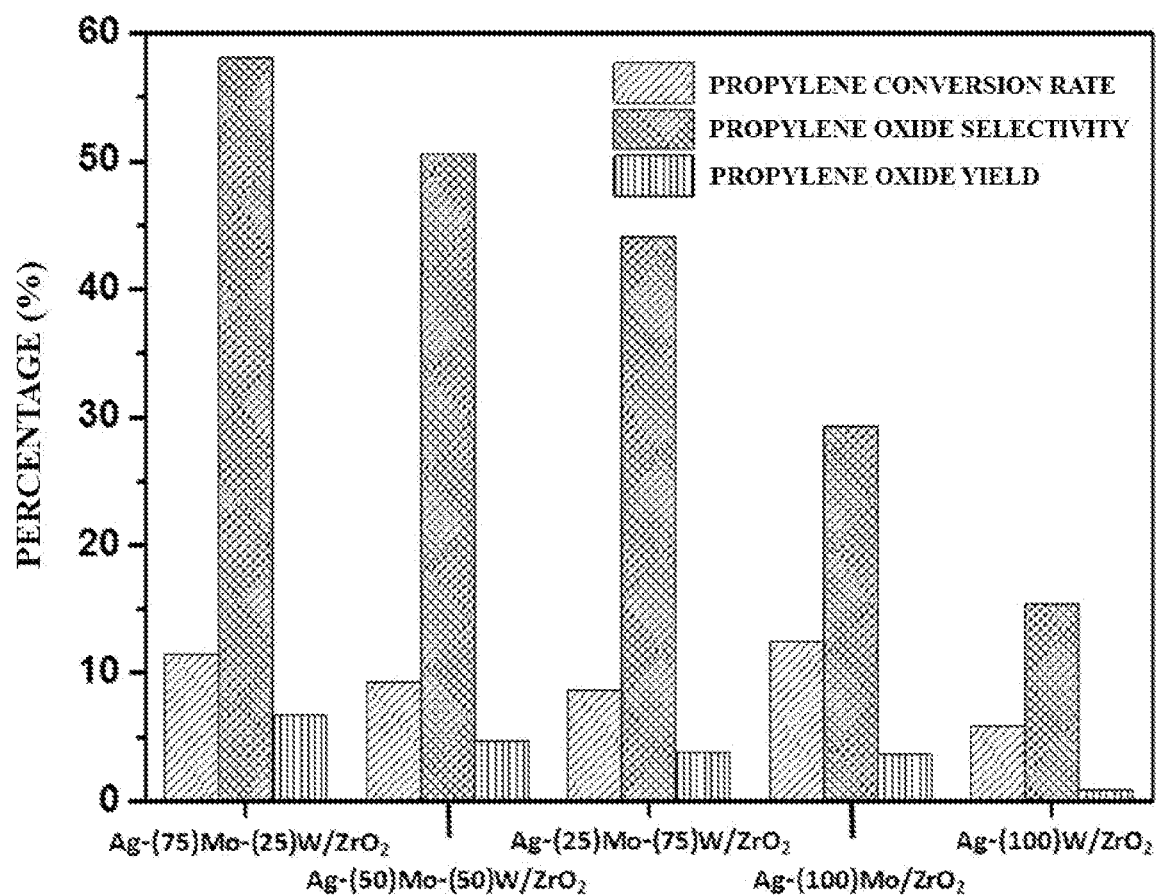
FIG. 4 is a graph showing a propylene conversion rate, a propylene oxide selectivity and a propylene oxide yield measurement result in Experimental Example 2 of the present invention.

Referring to FIG. 4 and Table 2, the measured values of both the propylene oxide selectivity and propylene oxide yield were high in Examples 1-3 in which a molybdenum oxide and a tungsten oxide were used together as promoters, and in particular, Example 1 showed the highest selectivity and propylene oxide yield. Specifically, as the tungsten oxide fraction was increased, the propylene conversion rate was somewhat decreased; and as the molybdenum oxide fraction was increased, the propylene oxide selectivity was increased. In particular, when the ratio of the molybdenum oxide to the tungsten oxide is 75:25 (Ag-(75)Mo-(25)W/ZrO₂), it can be confirmed that the propylene oxide selectivity and propylene oxide yield were further improved than the case of using the catalyst in which only the molybdenum oxide or tungsten oxide was introduced alone as the promoter (Ag-(100)Mo/ZrO₂, Ag-(100)W/ZrO₂).

Experimental Example 3

Experiments were performed in the same manner as in Experimental Example 2 except that the catalyst prepared according to the Example 1 was used and the temperatures of the reactor were adjusted to 350° C., 400° C., 460° C. or 500° C. The results were shown in Table 3 below.

TABLE 3

| Reaction rate | Propylene conversion rate (%) | Propylene oxide selectivity (%) | Propylene oxide yield (%) |
|---|---|---|---|
| 350° C. | 1.6 | 65.7 | 1.05 |
| 400° C. | 4.7 | 61.3 | 2.88 |
| 450° C. | 11.5 | 58.1 | 6.68 |
| 500° C. | 19.7 | 47.8 | 9.41 |

Referring to Table 3, a propylene oxide yield tended to increase as a reaction temperature increased. Specifically, when the reaction temperature was 400° C. or lower, it can be seen that the propylene oxide selectivity was high but the propylene conversion rate was low so that the overall yield was not high. On the other hand, when the reaction temperature was higher than 400° C., it was confirmed that the propylene conversion rate, propylene oxide selectivity, and propylene oxide yield were all excellent.

Preparation Example: Preparation of Zirconium Oxide (ZrO₂ (pH X)) Support Using Precipitation Method The zirconium oxide support was prepared by using the precipitation method. To prepare the zirconium oxide support, 9.2492 g of zirconium nitrate was dissolved in distilled water (500 ml) to prepare a zirconium oxide precursor solution. Then, when the precursor was completely dissolved, an ammonia aqueous solution having a concentration of 28-30 wt % was injected into the precursor solution at a rate of 60 ml/h.

At this point, the aqueous ammonia solution was injected such that the pH of the solution was 3, 6, 10, 12 or 14. Thereafter, this solution was stirred at a temperature of 25° C. and at an atomizer rotational speed of 5000 rpm for about 6 hours. Afterwards, the precipitate generated in the metal precursor solution was washed with distilled water while being filtered under reduced pressure to thereby remove the remaining aqueous ammonia solution, and then washed again with ethanol to prevent shrinkage caused by drying. Then, the washed precipitate was dried in an oven at 100° C. for 24 hours. Then, the precipitate was made into a powder form, heated to a temperature of 600° C. in an air atmosphere at a rate of 5° C. per minute, and then maintained and calcinated for 6 hours. The support thus prepared was named $ZrO_2$ (pH X) (X=3, 6, 10, 12, and 14), where X was the pH of the solution.

Example 4

A catalyst was prepared by using a slurry method as follows. 6 ml of distilled water, 0.9 ml of ethylenediamine and 1.63 g of oxalic acid were put into a beaker, and then 1 g of oxide ($Ag_2O$) was input and mixed. Then, after a silver precursor was completely dissolved, 0.1725 g of ammonium molybdate (($NE_4)_2MoO_4$) and 0.0575 g of ammonium (para)tungstate (($NH_4$) $10H_2(W_2O_7)_6 \cdot xH_2O$) were introduced into a solvent in which the silver precursor was dissolved such that a weight ratio of the sum of a molybdenum oxide ($MoO_3$) and a tungsten oxide ($WO_3$) to the total weight of the finally prepared catalyst was fixed to 5 wt %, and then a weight ratio of the molybdenum oxide to the tungsten oxide was 75:25. Thereafter, 3.54 g of the zirconium oxide $ZrO_2$ (pH 3) prepared in the above Preparation Example was introduced to obtain a slurry material, and the slurry was then stirred at 60° C. until the water was evaporated, so that a solid material remained. Then, the solid material was further dried in an oven at 120° C. for 24 hours. Then, the dried solid material was made into a powder form, heated to 460° C. in an air atmosphere at a rate of 5° C. per minute, and then maintained and calcinated for 3 hours to prepare a silver-molybdenum oxide-tungsten oxide/zirconium oxide catalyst (Ag-(75)Mo-(25) W/$ZrO_2$ (pH 3)).

Example 5

Except that the zirconium oxide, $ZrO_2$ (pH 6), prepared in the above Preparation Example was introduced, a catalyst was prepared in the same manner as in Example 4 to prepare a silver-molybdenum oxide-tungsten oxide/zirconium oxide catalyst (Ag-(75)Mo-(25)W/$ZrO_2$ (pH 6)).

Example 6

Except that the zirconium oxide $ZrO_2$ (pH 10) prepared in the above Preparation Example was introduced, a catalyst was prepared in the same manner as in Example 4 to prepare a silver-molybdenum oxide-tungsten oxide/zirconium oxide catalyst (Ag-(75)Mo-(25)W/$ZrO_2$ (pH 10)).

Example 7

Except that the zirconium oxide $ZrO_2$ (pH 12) prepared in the above Preparation Example was introduced, a catalyst was prepared in the same manner as in Example 4 to prepare a silver-molybdenum oxide-tungsten oxide/zirconium oxide catalyst (Ag-(75)Mo-(25)W/$ZrO_2$ (pH 12)).

Example 8

Except that the zirconium oxide $ZrO_2$ (pH 14) prepared in the above Preparation Example was introduced, a catalyst was prepared in the same manner as in Example 4 to prepare a silver-molybdenum oxide-tungsten oxide/zirconium oxide catalyst (Ag-(75)Mo-(25)W/$ZrO_2$ (pH 14)).

Experimental Example 4: Characterization Analysis and Comparison of Catalysts in which Silver-Molybdenum-Tungsten Oxide Introduced into Zirconium Oxide Support Produced by Precipitation Method Table 4 below shows summarization of the results of the nitrogen adsorption-desorption experiments of $ZrO_2$ (pH X) (X=3, 6, 10, 12, and 14) supports and Ag-(75)Mo-(25)W/$ZrO_2$ (pH X) (X=3, 6, 10, 12, and 14) catalysts prepared by the above-described Preparation Example and Examples 4-8.

TABLE 4

| Support | Specific surface area ($m^2/g$) | Pore volume ($cm^3/g$) | Catalyst | Specific surface area ($m^2/g$) | Pore volume ($cm^3/g$) |
|---|---|---|---|---|---|
| $ZrO_2$ (pH 3) | 23.5 | 0.07 | Ag-(75)Mo-(25)W/$ZrO_2$ (pH 3) | 12.4 | 0.03 |
| $ZrO_2$ (pH 6) | 23.0 | 0.07 | Ag-(75)Mo-(25)W/$ZrO_2$ (pH 6) | 11.2 | 0.02 |
| $ZrO_2$ (pH 10) | 22.1 | 0.06 | Ag-(75)Mo-(25)W/$ZrO_2$ (pH 10) | 12.1 | 0.02 |
| $ZrO_2$ (pH 12) | 21.9 | 0.06 | Ag-(75)Mo-(25)W/$ZrO_2$ (pH 12) | 11.3 | 0.02 |
| $ZrO_2$ (pH 14) | 24.7 | 0.07 | Ag-(75)Mo-(25)W/$ZrO_2$ (pH 14) | 12.9 | 0.03 |

From Table 4 it was analyzed that the support prepared had a specific surface area of 21-25 $m^2g^{-1}$, and a pore volume of about 0.07 $cm^3g^{-1}$. In addition, it was analyzed that the specific surface area of the catalyst was 11-13 $m^2g^{-1}$ and the pore volume thereof was about 0.02 $cm^3g^{-1}$. It can be found that the catalysts prepared via the same were formed in a form in which a pore structure was hardly developed.

Figure 5:
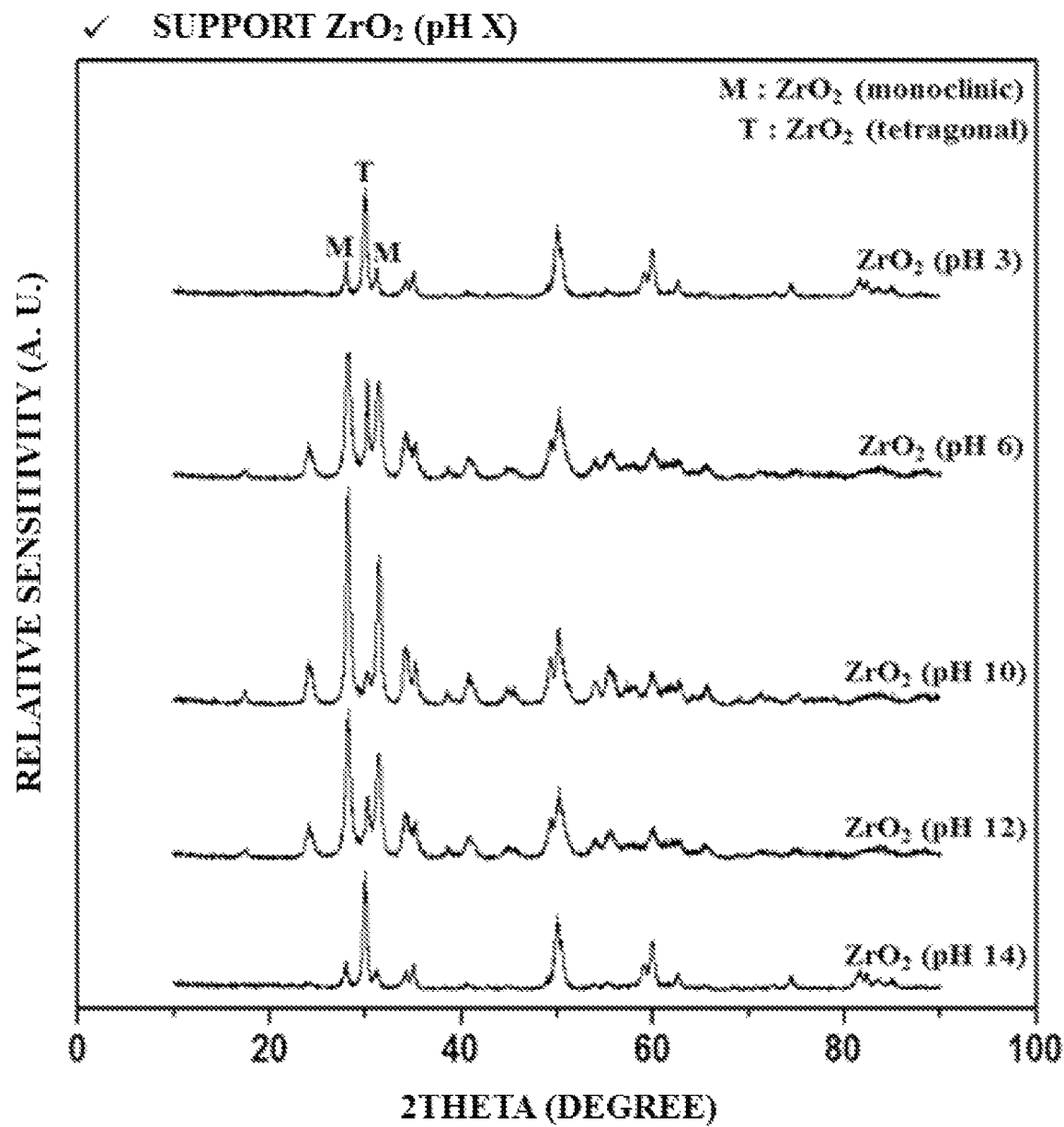
FIG. 5 is a graph showing results of X-ray diffraction analysis of a zirconium oxide support prepared in Preparation Example of the present invention.
Figure 6:
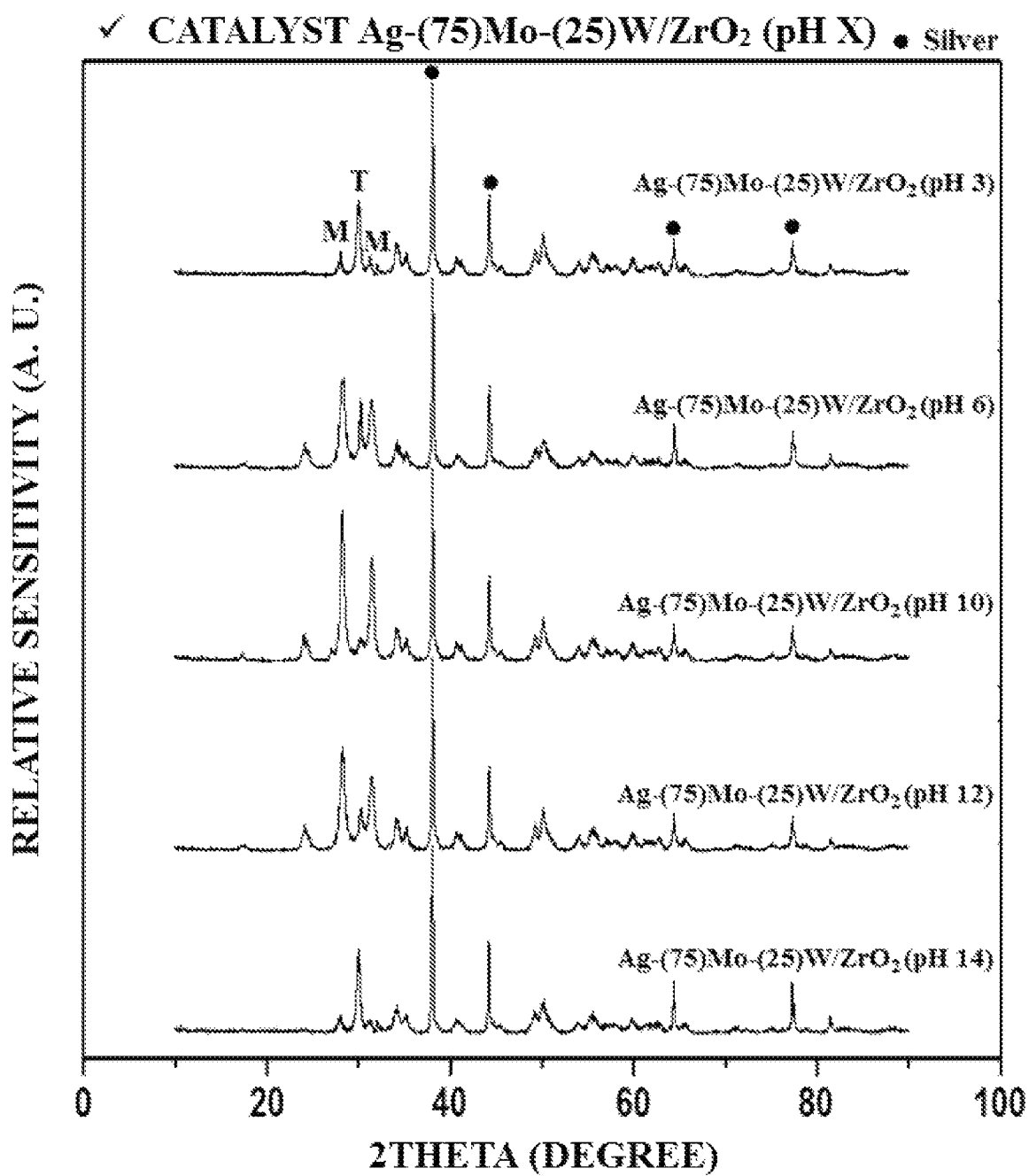
FIG. 6 is a graph showing results of X-ray diffraction analysis of catalysts prepared in Examples 4 to 8 of the present invention.

Meanwhile, FIGS. 5 and 6 are graphs showing the X-ray diffraction analysis results of the $ZrO_2$ (pH X) (X=3, 6, 10, 12, and 14) support and the Ag-(75)Mo-(25)W/$ZrO_2$ (pH X) (X=3, 6, 10, 12, 14) catalyst. First, it can be observed that the prepared supports had zirconium oxide monoclinic crystal phase peaks at around 2θ=28.2° and 31.4° and the zirconium oxide tetragonal crystal phase peak at around 2θ=30.2°. Here, it can be confirmed that the existence ratio of the monoclinic crystal phase to tetragonal crystal phase was changed depending on the pH during the preparation of the zirconium oxide support, and it can be found that the monoclinic crystal phase was best developed at a pH of 10. In addition, all of the prepared catalysts showed silver's inherent metal peaks at around 2θ=38°, 44°, 64° and 77°, and did not show characteristic peaks with respect to the molybdenum oxide and the tungsten oxide.

From the X-ray diffraction analysis results of the $ZrO_2$ (pH X) (X=3, 6, 10, 12, and 14), the ratio of the monoclinic crystal phase to the tetragonal crystal phase was quantified and shown in Table 5 below. Here, the fraction of the monoclinic crystal phase existing in the zirconium oxide support was calculated by <monoclinic crystal phase peak height/(monoclinic crystal phase peak height+tetragonal crystal phase peak height)>. As a result, it was shown that the fraction of monoclinic crystal phase changed in a volcano-like form in which the fraction increased and then decreased as the pH increased. In particular, it was shown that $ZrO_2$ (pH 10) has the highest monoclinic crystal phase fraction.

TABLE 5

| ZrO$_2$ (pH X) support | Fraction of monoclinic crystal phase |
|---|---|
| ZrO$_2$ (pH 3) | 0.38 |
| ZrO$_2$ (pH 6) | 0.59 |
| ZrO$_2$ (pH 10) | 0.91 |
| ZrO$_2$ (pH 12) | 0.79 |
| ZrO$_2$ (pH 14) | 0.19 |

* The ratio of the peak height (M/M + T) was used to estimate the fraction of monoclinic phase of zirconia. (M: monoclinic phase/T: tetragonal phase)

Figure 7:
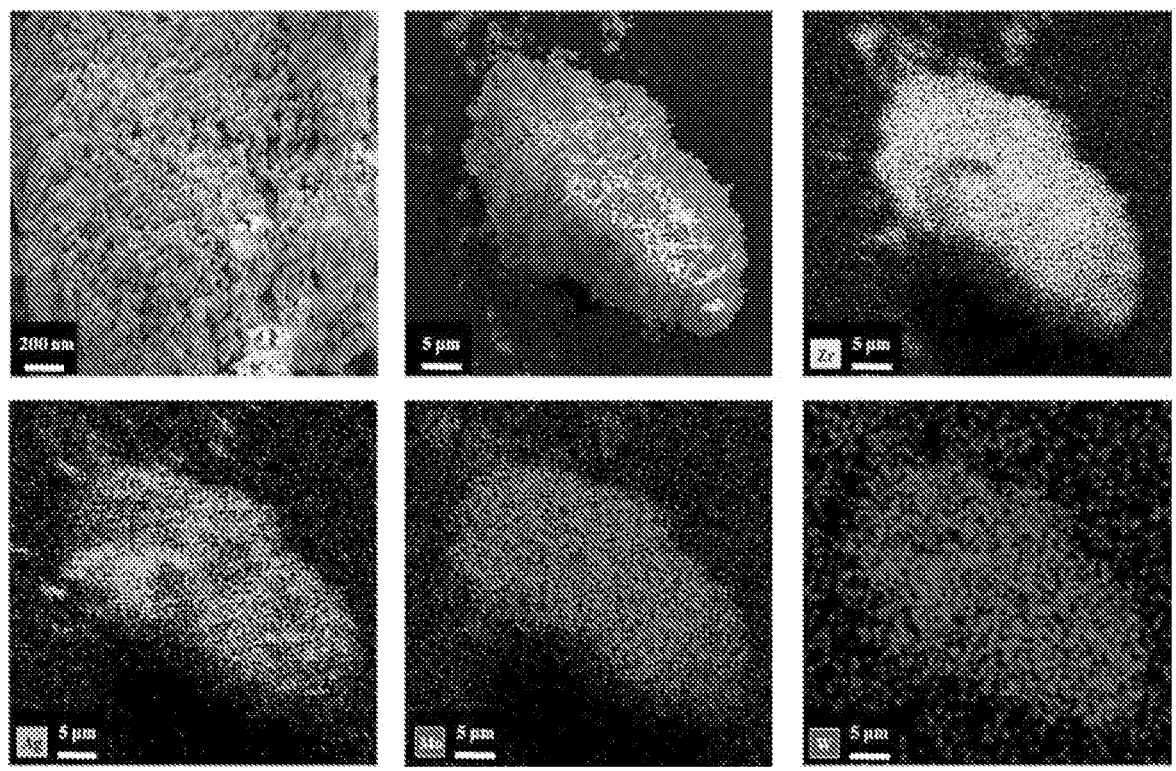
FIG. 7 is photographs (Zr: zirconium, Ag: silver, Mo: molybdenum, W: tungsten) showing results of scanning electron microscopic image analysis of a catalyst prepared in Example 6 of the present invention.

Experimental Example 5: Scanning Electron Microscope Observation of Catalysts in Which Silver-Molybdenum-Tungsten Oxide Introduced Into Zirconium Oxide Support Produced by Precipitation Method FIG. 7 is a scanning electron microscope (SEM) image of the Ag-(75)Mo-(25)W/ZrO$_2$ (pH 10) catalyst prepared in Example 6 of the present invention. From the SEM image, it can be seen that silver particles, and molybdenum oxide and tungsten oxide particles were uniformly present on the zirconium oxide in a form in which the pore structure was hardly developed. In addition, it can be confirmed that silver (Ag), molybdenum (Mo), tungsten (W), zirconium (Zr) particles were uniformly dispersed without aggregation in one site of the prepared Ag-(75)Mo-(25)W/ZrO$_2$ (pH 10) catalyst.

Experimental Example 6

The propylene oxide preparation reaction was performed by the propylene direct oxidation reaction using the prepared catalysts according to the above-described Examples 4-8. A feed stream consisting of 16.7 vol % of propylene, 8.3 vol % of oxygen, and 75.0 vol % of nitrogen, as a reactant composition, was made pass through a catalyst layer of a quartz reactor, so that the propylene direct oxidation reaction was performed without additional promoting gases. At this point, the temperature of the reactor was 460° C. and the pressure was atmospheric pressure. A total flow rate of the reactant with respect to the mass of the catalyst was maintained at 3,000 ml/h$^{-1}$gcat$^{-1}$. The propylene conversion rate, propylene oxide selectivity, and propylene oxide yield were calculated by the above Equations 1-3, respectively, and the results were shown in FIG. 8 and Table 6 below.

TABLE 6

| Catalyst | Propylene conversion rate (%) | Propylene oxide selectivity (%) | Propylene oxide yield (%) |
|---|---|---|---|
| Ag-(75)Mo-(25)W/ZrO$_2$ (pH 3) | 14.0 | 51.0 | 7.14 |
| Ag-(75)Mo-(25)W/ZrO$_2$ (pH 6) | 14.7 | 53.0 | 7.79 |
| Ag-(75)Mo-(25)W/ZrO$_2$ (pH 10) | 13.4 | 67.7 | 9.07 |
| Ag-(75)Mo-(25)W/ZrO$_2$ (pH 12) | 13.9 | 56.3 | 7.82 |
| Ag-(75)Mo-(25)W/ZrO$_2$ (pH 14) | 11.7 | 47.6 | 5.57 |

Figure 8:
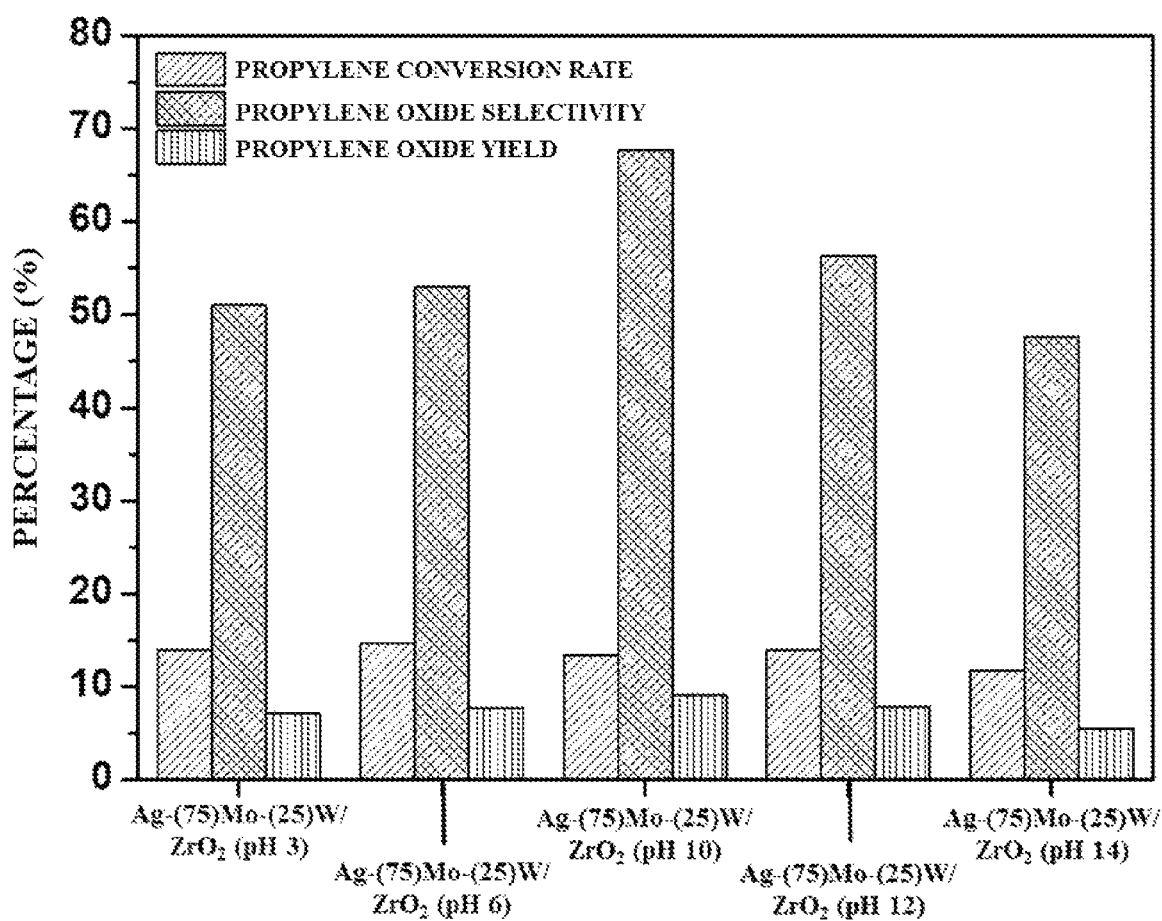
FIG. 8 is a graph showing a propylene conversion rate, A propylene oxide selectivity and A propylene oxide yield measurement result in Experimental Example 6 of the present invention.

Referring to FIG. 8 and Table 6, both the propylene oxide selectivity and propylene oxide yield changed in a volcano-like form in which that the propylene oxide selectivity and propylene oxide yield increased and then decrease depending on the pH at the time of preparation of the zirconium oxide support. In particular, the Ag-(75)Mo-(25) W/ZrO$_2$ (pH 10) catalyst showed the highest propylene oxide selectivity and propylene oxide yield.

It can be found that the results of Experimental Example 6 using the zirconium oxide support prepared through precipitation according to the method of the above Preparation Example were more excellent than those of Experimental Example 2 using the commercially available zirconium oxide support.

Figure 9:
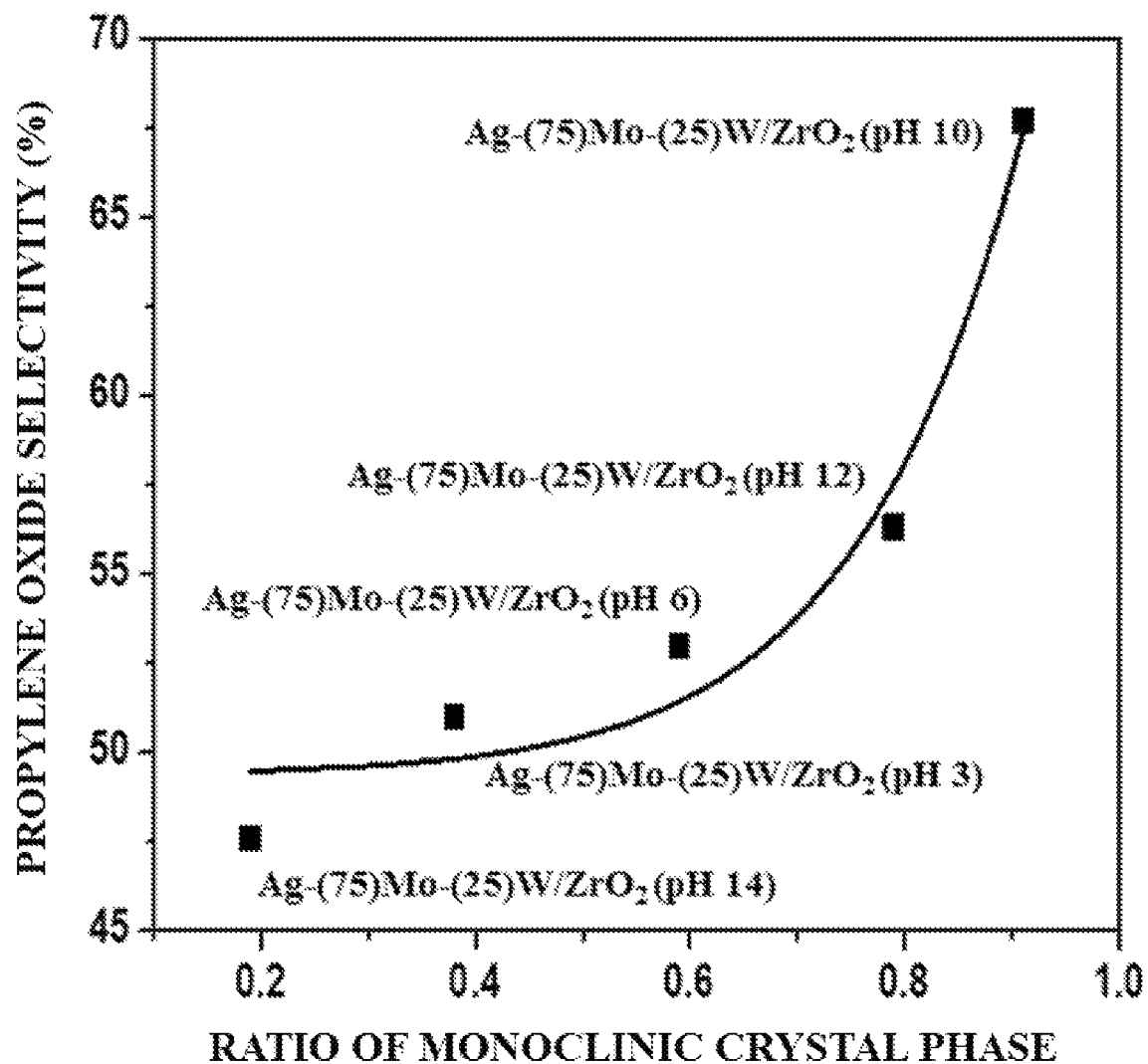
FIG. 9 is a graph showing correlation of propylene oxide selectivity according to monoclinic crystal phase fractions of catalysts prepared in Examples 4 to 8 of the present invention.

However, FIG. 9 is a graph showing a correlation of the propylene oxide selectivity according to the monoclinic crystal phase fraction of Ag-(75)Mo-(25)W/ZrO$_2$ (pH X)(X=3, 6, 10, 12, and 14) catalyst. Referring to FIG. 9, it can be confirmed that the propylene oxide selectivity increases as monoclinic crystal phase ratio increases, and, in particular, it can be confirmed that the highest monoclinic crystal phase fraction and propylene oxide selectivity appears in the Ag-(75)Mo-(25)W/ZrO$_2$ (pH 10) catalyst. From these results, it can be found that the characteristics of the zirconium oxide, which is a support, affect the propylene direct oxidation reaction, and there is a zirconium oxide support preparation condition that leads to a dramatic improvement in catalytic activity.

The preferred embodiments of the present invention have been described in detail above. The description of the present invention is intended to be illustrative, and those having ordinary skill in the technical field to which the present invention belongs may understand that other concrete shapes may be easily modified without changing the technical idea and essential features of the present invention.

Therefore, the scope of the present invention is not limited by the above detailed description, but is defined by the scope of the following claims, and all alterations or modified forms derived from the meanings, ranges and equivalent concepts of the claims should be interpreted as being included in the scope of the present invention.

The invention claimed is:

1. A propylene direct oxidation reaction catalyst, which is a supported silver catalyst used for preparing a propylene oxide from a propylene direct oxidation reaction, the catalyst comprising, as a catalyst promoter, a molybdenum oxide (MoO$_3$) and a tungsten oxide (WO$_3$), wherein a carrier used for the supported silver catalyst is a zirconium oxide, and wherein the zirconium oxide has a monoclinic crystal phase fraction of 0.15-1.00 as calculated based on X-ray diffraction analysis results according to the following equation:

Monoclinic crystal phase peak height/(monoclinic crystal phase peak height+tetragonal crystal phase peak height)     (Equation).

2. The propylene direct oxidation reaction catalyst of claim 1, wherein the silver is included in an amount of 5-30% by weight with respect to the entire catalyst.

3. The propylene direct oxidation reaction catalyst of claim 1, wherein the promoter is included in an amount of 1-20% by weight with respect to the entire catalyst.

4. The propylene direct oxidation reaction catalyst of claim 1, wherein the molybdenum oxide to the tungsten oxide is included, by weight percentage, at a ratio of 1:99 to 99:1.

5. The propylene direct oxidation reaction catalyst of claim 1, wherein the zirconium oxide is prepared according to a method comprising the steps of:
(i) dissolving a zirconium oxide precursor in a solvent to prepare a zirconium oxide precursor solution;

(ii) adding a basic aqueous solution to the zirconium oxide precursor solution to prepare a first solution;

(iii) stirring the first solution prepared in the step (ii) and then filtering to obtain a solid precipitate; and (iv) drying the solid precipitate to obtain a solid material.

6. A method for preparing the propylene direct oxidation reaction catalyst of claim 1, the method comprising:

(a) dissolving a silver precursor in a solvent to prepare a silver precursor solution;

(b) dissolving, in the silver precursor solution, a molybdenum oxide precursor and a tungsten oxide precursor as a metal oxide precursor to prepare a silver-metal oxide precursor solution;

(c) adding a zirconium oxide to the silver-metal oxide precursor solution to prepare a silver-metal oxide precursor/zirconium oxide slurry; and (d) stirring the slurry to form an obtained solid material, then drying the slurry and heat treating the obtained solid material to prepare the catalyst.

7. The method of claim 6, wherein the solvent is a mixed aqueous solution of water and at least one organic solvent selected from the group consisting of amines, acids and glycols.

8. The method of claim 6, wherein the silver precursor is at least one selected from the group consisting of silver oxide, silver nitrate, silver carbonate, silver acetate, silver oxalate, silver lactate, silver citrate and silver propionate.

9. The method of claim 6, wherein the molybdenum oxide precursor and the tungsten oxide precursor are each independently at least one selected from the group consisting of a nitrate-based precursor, a chloride-based precursor, an acetate-based precursor, and an ammonium-based precursor.

10. The method of claim 6, wherein the zirconium oxide is prepared according to a method comprising the steps of:

(i) dissolving a zirconium oxide precursor in a solvent to prepare a zirconium oxide precursor solution;

(ii) adding a basic aqueous solution to the zirconium oxide precursor solution to prepare a first solution;

(iii) stirring the first solution prepared in the step (ii) and then filtering to obtain a solid precipitate; and (iv) drying the solid precipitate to obtain a solid material.

11. The method of claim 10, wherein the zirconium oxide precursor is at least one selected from the group consisting of a nitrate-based precursor, a chloride-based precursor, a bromide-based precursor, an acetate-based precursor, and an acetylacetonate-based precursor.

12. The method of claim 10, wherein the solvent is any one selected from the group consisting of water, an alcohol having 1-4 carbon atoms, and a mixture thereof.

13. The method of claim 10, wherein the step (ii) includes adding a basic aqueous solution to adjust the pH of the zirconium oxide precursor solution to 3 to 14.

14. The method of claim 6, wherein the heat treating of the obtained solid material is performed at 100-600° C. for 1-8 hours.

15. A method for preparing a propylene oxide through a propylene direct oxidation reaction catalyst in the presence of the catalyst of claim 1, the method comprising conducting direct oxidation of propylene.

16. The method of claim 15, wherein the direct oxidation of propylene is performed under conditions in which: among total raw materials, the propylene is contained in an amount of 10-50 vol %, oxygen is contained in an amount of 5-25 vol % and inert gas is contained in an amount of 25-85 vol %; and a gas hourly space velocity (GHSV) is 1,000-20,000 $h^{-1}$.

17. The method of claim 15, wherein the propylene direct oxidation reaction is performed at a temperature of 300-600° C. under a pressure of atmospheric pressure to 50 atm.

* * * * *